United States Patent [19]
Genaro

[11] Patent Number: 5,300,053
[45] Date of Patent: Apr. 5, 1994

[54] ABSORBENT BRIEF

[75] Inventor: Donald M. Genaro, Haworth, N.J.

[73] Assignee: Henry Dreyfuss Associates, New York, N.Y.

[21] Appl. No.: 787,251

[22] Filed: Nov. 4, 1991

[51] Int. Cl.⁵ .......................................... A61F 13/15
[52] U.S. Cl. .................. 604/378; 604/385.1; 604/380
[58] Field of Search ............... 609/378, 355, 392, 393, 609/397, 385.1, 385.2, 380

[56] References Cited

U.S. PATENT DOCUMENTS

| | | | |
|---|---|---|---|
| 3,065,751 | 11/1962 | Gobbo | 128/287 |
| 3,343,543 | 9/1967 | Glassman | 128/290 |
| 3,411,504 | 11/1968 | Glassman | 128/290 |
| 3,766,922 | 10/1973 | Krusko | 128/284 |
| 3,769,978 | 11/1973 | DeNight et al. | 128/287 |
| 3,889,679 | 6/1975 | Taylor | 604/378 |
| 3,890,973 | 6/1975 | Davis et al. | 604/355 |
| 3,897,784 | 8/1975 | Fitzgerald | 128/290 R |
| 4,027,672 | 6/1977 | Karami | 604/380 |
| 4,079,739 | 3/1978 | Whitehead | 128/290 R |
| 4,265,245 | 5/1981 | Glassman | 128/287 |
| 4,443,512 | 4/1984 | Delvant | 604/380 |
| 4,624,666 | 11/1986 | DeRossett et al. | 604/366 |
| 4,650,481 | 3/1987 | O'Connor et al. | 604/380 |
| 4,662,876 | 5/1987 | Wiegner | 604/380 |
| 4,678,464 | 7/1987 | Holtman | 604/385 R |
| 4,678,464 | 7/1987 | Holtman | 604/380 |
| 4,704,112 | 11/1987 | Suzuki et al. | 604/380 |
| 4,731,065 | 3/1988 | Yamada | 604/355 |
| 4,738,675 | 4/1988 | Buckley et al. | 604/380 |
| 4,758,240 | 7/1988 | Glassman | 604/379 |
| 4,781,710 | 11/1988 | Megison et al. | 604/378 |
| 4,834,735 | 5/1989 | Alemany et al. | 604/368 |
| 4,892,535 | 1/1990 | Bjornberg et al. | 604/380 |
| 4,990,147 | 2/1992 | Freeland | 604/385.2 |
| 5,013,309 | 5/1991 | Baiggs, Jr. et al. | 604/381 |
| 5,019,070 | 5/1991 | Ruben | 604/387 |
| 5,019,070 | 5/1991 | Ruben | 604/387 |
| 5,047,023 | 9/1991 | Berg | 604/368 |
| 5,062,840 | 11/1991 | Holt et al. | 604/385.1 |
| 5,151,091 | 9/1992 | Glang et al. | 604/385.1 |
| 5,207,665 | 5/1993 | Davis et al. | 604/399 |

*Primary Examiner*—David Isabella
*Assistant Examiner*—Gina M. Gualtieri
*Attorney, Agent, or Firm*—Fitzpatrick, Cella, Harper & Scinto

[57] ABSTRACT

An absorbent brief, or diaper, including a liquid-permeable layer, a liquid-impervious layer, and an absorbent layer sandwiched between the liquid-permeable and liquid-impervious layers, the absorbent layer having a dispersion channel extending through the absorbent layer to the liquid-impervious layer for providing unobstructed liquid flow.

31 Claims, 2 Drawing Sheets

ABSORBENT BRIEF

BACKGROUND OF THE INVENTION

1. Field of the Invention

The present invention relates generally to personal hygiene products. More particularly, it relates to an absorbent brief structure, for example a diaper, and to means for reducing the tendency of the brief to leak during evacuation of a large volume of liquid over a short period of time.

2. Brief Description of the Prior Art

Incontinence, or the inability to control excretory functions, is a common condition, particularly in infants and the elderly. Every child and, according to recent studies, as many as one-third of older adults have some problem with urinary incontinence, which among older persons is more common among those who are housebound or have cognitive or functional impairments.

Incontinence among the elderly may have severe consequences. For example, incontinent individuals may restrict their physical or social activities and may exhibit a preoccupation with toileting functions. Incontinence also can cause psychological reactions, can result in considerable expense for cleaning, and can precipitate institutionalization or even death.

Although many older incontinent persons could be cured, many tend to view their condition merely as embarrassing, and prefer to rely on self-devised strategies to minimize urine loss. These strategies typically include the use of absorbent briefs or pads.

Absorbent briefs, also known as adult diapers, are well known for use by incontinent persons. These briefs typically include a first or inner layer made of a liquid-permeable material, a second or outer layer made of a liquid-impervious material, and an absorbent layer sandwiched between the inner and outer layers. The inner layer, which is generally worn next to the body, allows liquid to penetrate therethrough to the absorbent layer. The outer layer provides a barrier that prevents liquid from penetrating through the brief, e.g., to bedding, clothing, or the like. Although such absorbent briefs provide satisfactory use in many instances, these briefs often leak, particularly in or around the crotch area, in the case of a large liquid evacuation over a short period of time.

Various structures for absorbent briefs and pads have been suggested for improving absorption of quick, large volume, liquid evacuations, and for reducing the associated leaking. One suggestion is merely to increase the volume of the absorbent layer. Another suggestion is to use a material having a greater absorbency (assuming the same volume). The former increases the volume of the brief and may become awkward, uncomfortable or embarrassing to the user (e.g., unsightly). The latter may be too expensive.

U.S Pat. No. 4,678,464 relates to an absorbent structure (e.g., a diaper, a sanitary pad, an incontinence pad or the like) that contains a loosely compacted cellulosic fibrous batt having two reservoirs and a connecting channel formed by compressing the fibrous batt. The base of each reservoir is formed by a densified fibrous region, and the fibrous base of the channel is of a higher density than the immediate surrounding areas, except for the reservoirs.

SUMMARY OF THE PRESENT INVENTION

The present invention provides an improved absorbent brief structure that includes a substantially liquid-impervious layer, and an absorbent layer having one or more dispersion channels that are cut through the absorbent layer to the substantially liquid-impervious layer. The dispersion channel includes walls that define the channel in the absorbent layer to provide substantially unobstructed flow of a large volume of liquid from one portion of the absorbent layer to another portion of the absorbent layer, thereby increasing the rate of absorption and reducing leakage.

In another aspect of the present invention, the through-cut dispersion channel is formed longitudinally in at least a crotch portion of the brief. The dispersion channel may be formed symmetrically about the longitudinal axis of the brief.

In another aspect of the present invention, the through-cut dispersion channel includes a primary portion formed longitudinally in the crotch area of the brief, and at least one secondary portion formed in at least a portion of either a front panel or a rear panel of the brief. The secondary portion may include a pair of channel branches forming a Y-shaped dispersion channel with the primary portion.

In yet another aspect of the present invention, the absorbent brief may include two or more dispersion channels formed therein, each dispersion channel defining a through-hole therein. The two or more dispersion channels may be symmetrically arranged in a parallel configuration along a longitudinal axis of the brief.

BRIEF DESCRIPTION OF THE DRAWINGS

A more complete appreciation of the present invention and the many attendant advantages thereof readily will be apparent with reference to the following detailed description of a preferred embodiment and the accompanying drawings, wherein.

DETAILED DESCRIPTION OF A PREFERRED EMBODIMENT

Figure 1:
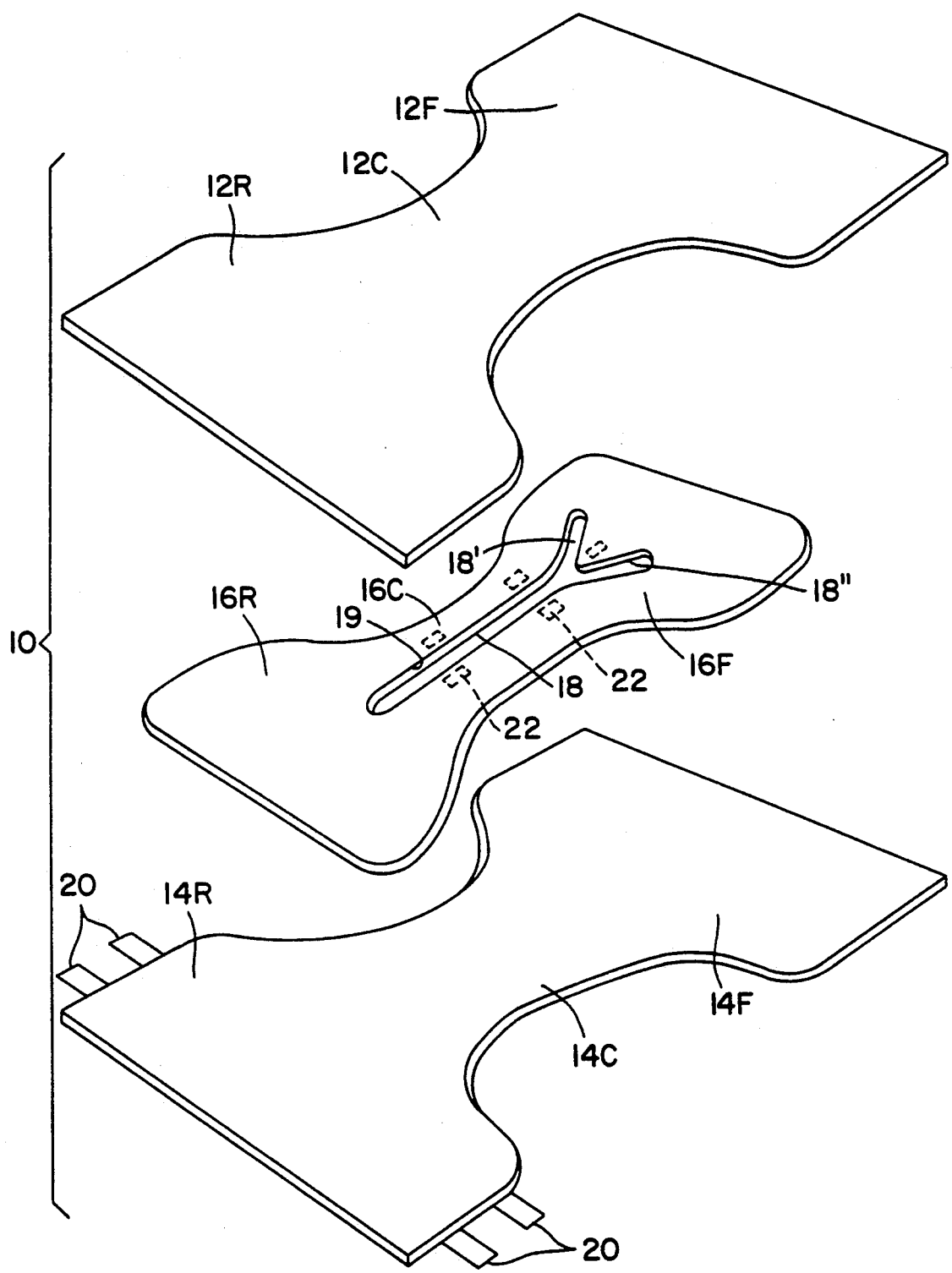
FIG. 1 is an exploded view of an embodiment of the present invention, including an absorbent brief having a Y-shaped dispersion channel formed in an absorbent layer thereof.

Referring now to the drawings, wherein like reference numerals correspond to like or similar elements throughout, FIG. 1 illustrates by example an absorbent brief of the present invention As shown therein, brief 10 generally includes a first or inner layer 12, a second or outer layer 14, and an absorbent layer 16 disposed between inner layer 12 and outer layer 14 and having a dispersion channel 18 formed therein.

As shown in FIG. 1, brief 10 preferably is preformed in a conventional hour-glass shape, having a front panel (including respective front layer panels 12F, 14F, 16F), a rear panel (including respective rear layer panels 12R, 14R, 16R) and a crotch panel (including respective crotch layer panels 12C, 14C, 16C). Brief 10 also may include tabs 20 for securing the rear panel to the front panel proximate a person's waist, when folded to conform to the person's crotch and buttocks. Tabs 20 may be formed of any conventional construction, such as adhesive tape, velcro or snaps, as is well known in the art.

Inner layer 12 generally may be composed of a conventional liquid-permeable material, and is most preferably composed of a lightweight, non-woven, liquid-permeable material which is non-irritating to human skin, such as is known in the art. Likewise, outer layer 14 generally may be composed of a conventional material that is substantially liquid-impervious, and most preferably is composed of a lightweight, liquid-impervious material, such as is known in the art.

Absorbent layer 16 may be composed of any conventional absorbent material suitable for use in an absorbent brief. The absorbent layer 16 preferably is a loosely compacted cellulosic batt formed from wood pulp fibers, rayon fibers, cotton liners or mixtures thereof, the batt primarily being held together by interfiber bonds requiring no added adhesive. In some instances, the batt may contain synthetic fusible fibers such as polyethylene, polypropylene and the like. However, the batt preferably is a coherent web of a loosely-compacted cellulosic fibers, most preferably comminuted wood pulp fibers in the form of so-called "fluff."

Dispersion channel 18 is an absorbent free channel defined by channel walls 19 of absorbent layer 16, and provides one or more through-holes in absorbent layer 16. In one embodiment, as shown in FIG. 1, dispersion channel 18 is a Y-shaped channel cut through layer 16 that extends along a longitudinal axis of brief 10, from the rear panel to the front panel. More specifically, a primary portion or leg of dispersion channel 18 runs longitudinally along the axis of crotch panel 16C, while a secondary portion of dispersion channel 18, including two legs or branches 18',18'', is formed in front panel 16F. Of course, a secondary portion alternatively may be formed in the rear panel, or both in the front and rear panels. Also, the secondary portion may be arranged in any number of shapes, including an open-loop configuration, a U-shaped configuration, or the like, depending on the application. Finally, dispersion channel 18 preferably is formed symmetrically about the longitudinal axis of brief 10. Those skilled in the art readily will appreciate numerous variations of structure for the primary and secondary channel portions. Dispersion channel 18 may be formed by any conventional manufacturing method. For example, it may be formed by cutting through a preformed absorbent layer. Alternatively, an absorbent layer may be prepared having a dispersion channel 18 preformed therein. In each case, the dispersion channel 18 formed during manufacturing provides an unobstructed channel extending through layer 16 to outer layer 14. When absorbent brief 10 is worn, it may be folded and crumpled such that portions of the dispersion channel 18 may assume a partially collapsed configuration, e.g., channel walls 19 on opposite sides of dispersion channel 18 may be pressed together due to a folding or sheering motion between opposite sides of channel walls 19. The amount of collapse may vary depending on the position of the person wearing the brief, e.g., sitting, laying on back, laying on side, etc. Therefore, in some instances it may be preferable to secure absorbent layer 16 relative to either or both of liquid-permeable layer 12 and liquid-impervious layer 14. Securing absorbent layer 16 relative to one or both of these layers may be achieved by any conventional method, e.g., by tacking the adjacent layers together with an adhesive glue. (See, e.g.. adhesive glue tacks 22, shown in phantom in FIG. 1.) For purposes of the present invention, all such configurations of dispersion channel 18 shall be deemed unobstructed, in that no physical structure is provided therein during manufacture.

Figure 2:
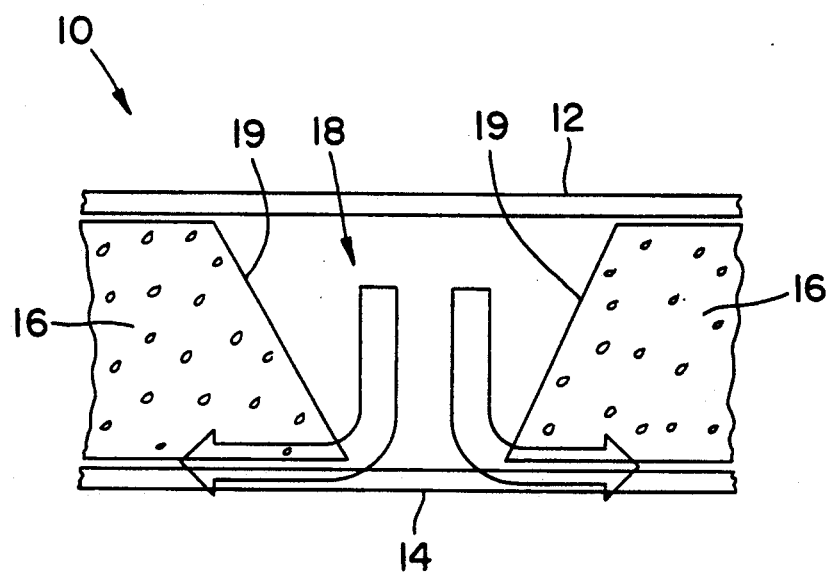
FIG. 2 is a cross-sectional view of the dispersion channel of FIG. 1.

Dispersion channel 18 provides for quick, high-volume flow of evacuated liquid from a point of impact to one or more areas of absorption. Specifically, a high volume of liquid incident on brief 10 will flow to distribution channel 18, and quickly be channeled thereby to other locations or areas of absorption within distribution channel 18, e.g., to secondary channel branches 18',18''. It will be appreciated that the structure of brief 10 facilitates quick distribution of a large volume of gushing liquid because dispersion channel 18 extends through layer 16. Gushing liquid channeled through it tends to flow along the smooth, non-absorbent surface of liquid-impervious layer 14. Referring to FIG. 2, which illustrates dispersion channel 18 in cross-section, since dispersion channel 18 extends through layer 16 to liquid-impervious layer 14, liquid will flow unobstructed thereto and also quickly distribute along the surface of layer 14 to adjacent areas of absorbent layer 16, as shown by flow arrows in the drawing. FIG. 2 also shows a taper in the walls of the channel in the vertical direction.

In another aspect of the present invention, dispersion channel 18 also constitutes a preselected fold area, so that when worn, brief 10 tends to assume a boat-shaped configuration or the like, to promote comfort, to reduce the risk of any liquid gushing to the perimeter of the brief, particularly in the crotch area prior to absorption, or to reduce any occlusion of the dispersion channel.

Although the present invention is described above in the context of a diaper or absorbent brief for an incontinent adult, it readily will be appreciated that the present invention equally is applicable to alternative personal hygiene product structures that have the property of containing quick, large volume impacts of liquids, including baby diapers, incontinent pads, and the like.

The width or size of dispersion channel 18 may vary depending on the particular application. For example, the width of dispersion channel 18 may be smaller in an infant diaper than in an adult diaper or incontinent pad. In the adult diaper or absorbent brief 10 of the preferred embodiment, the width of dispersion channel 18 preferably is in the range of about 0.25 inch to about 2 inches, most preferably about 0.75 inch. In addition, dispersion channel 18 may be tapered in its longitudinal or vertical directions, e.g., dispersion channel 18 may be provided with an end located in one of the front or rear panels, wherein dispersion channel 18 is tapered in a direction of that end. Those skilled in the art readily will be able to determine the optimal shape and size, or range of sizes, for providing quick, high-volume liquid flow and absorption in an given application.

Numerous other embodiments, variations and modifications will be apparent to those skilled in the art and all such other embodiments, variations and modifications fall within the scope of the invention herein described and are intended to be covered thereby. It will be appreciated that the above description of one embodiment is illustrative only, and is not intended to limit the scope of the present invention, which is defined by the following claims.

What is claimed is:

1. An absorbent brief, comprising:
   a layer formed of a substantially liquid-impervious material, and
   a liquid-absorbent layer disposed adjacent the liquid-impervious material layer, the liquid-absorbent layer having an absorbent-free dispersion channel which extends completely through the liquid-absorbent layer from a top surface of the liquid-absorbent layer through a bottom surface of the liquid-absorbent layer to said liquid-impervious material layer, the dispersion channel having a length and a width and providing for liquid flow along the length of the dispersion channel from a first through area of absorption of the liquid-absorbent layer to a second through area of absorption of the liquid-absorbent layer remote from the first through area, and the dispersion channel being in at least a front panel of the brief.

2. The absorbent brief of claim 1, the dispersion channel also being in at least a portion of a crotch panel of the brief.

3. The absorbent brief of claim 2, the dispersion channel also being in at least a portion of a rear panel of the brief.

4. The absorbent brief of claim 1, wherein the dispersion channel includes at least two channel branches in the front panel.

5. The absorbent brief of claim 1, further comprising a layer formed of a liquid-permeable material, the liquid-permeable layer being disposed adjacent the liquid-absorbent layer on a side opposite the liquid-impervious layer.

6. The absorbent brief of claim 5, wherein the liquid-impervious layer extends across the channel without extending into the channel.

7. The absorbent brief of claim 5, wherein the dispersion channel is located between the liquid-permeable layer and the substantially liquid-impervious layer.

8. The absorbent brief of claim 1, wherein the dispersion channel formed in the absorbent layer has a width in the range of 0.25 inches to 2 inches.

9. The absorbent brief of claim 8, wherein the width of the dispersion channel is about 0.75 inch.

10. The absorbent brief of claim 1, wherein the dispersion channel has a tapered width in a direction of its length.

11. The absorbent brief of claim 1, wherein the dispersion channel has a cross-section, and wherein a width of the cross-section is tapered in a direction from the top surface to the bottom surface of the liquid-absorbent layer.

12. The absorbent brief of claim 1, wherein means are provided for securing the liquid-absorbent layer relative to the liquid-impervious layer.

13. The absorbent brief of claim 6, wherein means are provided for securing the liquid-absorbent layer relative to at least one of the liquid-permeable layer and the liquid-impervious layer.

14. The absorbent brief of claim 1, wherein the first through area is located near a location of liquid evacuation of a wearer.

15. The absorbent brief of claim 3, wherein the first through area is located in a crotch panel of the brief and the second through area is located in at least one of a front panel and a rear panel of the brief.

16. The absorbent brief of claim 2, wherein the dispersion channel includes at least two channel branches in the front panel.

17. The absorbent brief of claim 3, wherein the dispersion channel includes at least two channel branches in the front panel.

18. The absorbent brief of claim 2, further comprising a layer formed of a liquid-permeable material, the liquid-permeable layer being disposed adjacent the liquid-absorbent layer on a side opposite the liquid-impervious layer.

19. The absorbent brief of claim 3, further comprising a layer formed of a liquid-permeable material, the liquid-permeable layer being disposed adjacent the liquid-absorbent layer on a side opposite the liquid-impervious layer.

20. The absorbent brief of claim 2, wherein the dispersion channel formed in the liquid-absorbent layer has a width in the range 0.25 inches to 2 inches.

21. The absorbent brief of claim 3, wherein the dispersion channel formed in the absorbent layer has a width in the range of 0.25 inches to 2 inches.

22. The absorbent brief of claim 20, wherein the width of the dispersion channel is about 0.75 inch.

23. The absorbent brief of claim 21, wherein the width of the dispersion channel is about 0.75 inch.

24. The absorbent brief of claim 2, wherein the dispersion channel has a tapered width in a direction of its length.

25. The absorbent brief of claim 3, wherein the dispersion channel has a tapered width in a direction of its length.

26. The absorbent brief of claim 2, wherein the dispersion channel has a thickness, and wherein the dispersion channel has a tapered width in a direction of tis thickness.

27. The absorbent brief of claim 3, wherein the dispersion channel has a thickness, and wherein the dispersion channel has a tapered width in a direction of its thickness.

28. The absorbent brief of claim 2, wherein means are provided for securing the liquid-absorbent layer relative to the liquid-impervious layer.

29. The absorbent brief of claim 3, wherein means are provided for securing the liquid-absorbent layer relative tot he liquid-impervious layer.

30. An absorbent brief, comprising:
a layer formed of a substantially liquid-impervious material, and
a liquid-absorbent layer disposed adjacent the liquid-impervious material layer, the liquid-absorbent layer having an absorbent-free dispersion channel which extends completely through the liquid-absorbent layer from a top surface of the liquid-absorbent layer through a bottom surface of the liquid-absorbent layer to said liquid-impervious material layer, the dispersion channel having a length and a width and providing for liquid flow along the length of the dispersion channel from a first through area of absorption of the liquid-absorbent layer to a second through area of absorption of the liquid-absorbent layer remote from the first through area, and the dispersion channel being in at least a front panel, a crotch panel and a rear panel of the brief, wherein at least one channel portion in the front panel or the rear panel includes two channel branches, and the at least one channel portion and the channel branches are arranged in a Y-shaped configuration.

31. An absorbent brief, comprising:
a layer formed of a substantially liquid-impervious material, and
a liquid-absorbent layer disposed adjacent the liquid-impervious material layer, the liquid-absorbent layer having an absorbent-free dispersion channel which extends completely through the liquid-absorbent layer from a top surface of the liquid-absorbent layer through a bottom surface of the liquid-absorbent layer to said liquid-impervious material layer, the dispersion channel having a length and a width and providing for liquid flow along the length of the dispersion channel from a first through area of the absorption of the liquid-absorbent layer to a second through area of absorption of the liquid-absorbent layer remote from the first through area, and the dispersion channel further having a first end terminating in a front panel of the brief and a second end terminating in a rear panel of the brief.

* * * * *